United States Patent
Takahashi et al.

(10) Patent No.: US 10,186,055 B2
(45) Date of Patent: Jan. 22, 2019

(54) DRR IMAGE GENERATION METHOD AND DRR IMAGE GENERATION APPARATUS

(71) Applicant: SHIMADZU CORPORATION, Nakagyo-Ku, Kyoto-Shi, Kyoto (JP)

(72) Inventors: Wataru Takahashi, Kyoto (JP); Shinichiro Mori, Chiba (JP)

(73) Assignee: SHIMADZU CORPORATION, Kyoto (JP)

(*) Notice: Subject to any disclaimer, the term of this patent is extended or adjusted under 35 U.S.C. 154(b) by 0 days.

(21) Appl. No.: 15/467,510

(22) Filed: Mar. 23, 2017

(65) Prior Publication Data
US 2018/0276851 A1 Sep. 27, 2018

(51) Int. Cl.
*G06T 11/00* (2006.01)
*A61B 6/03* (2006.01)
*A61B 6/00* (2006.01)
*A61N 5/10* (2006.01)

(52) U.S. Cl.
CPC .......... *G06T 11/003* (2013.01); *A61B 6/032* (2013.01); *A61B 6/461* (2013.01); *A61B 6/487* (2013.01); *A61B 6/5205* (2013.01); *A61B 6/54* (2013.01); *A61N 5/1077* (2013.01); *G06T 2210/41* (2013.01)

(58) Field of Classification Search
CPC ......... G06T 11/00; A61B 6/032; A61B 6/461; A61B 6/487; A61B 6/5205; A61B 6/54
See application file for complete search history.

(56) References Cited

U.S. PATENT DOCUMENTS

| | | | | |
|---|---|---|---|---|
| 7,653,226 B2 * | 1/2010 | Guhring | .................. | G06T 15/08 382/128 |
| 9,230,322 B2 * | 1/2016 | Hirai | ..................... | G06T 7/0012 |
| 9,683,948 B2 * | 6/2017 | Gao | ..................... | A61B 6/5258 |
| 9,734,574 B2 * | 8/2017 | Sugiura | .................. | G06T 7/0012 |
| 9,830,718 B2 * | 11/2017 | Hirai | ..................... | G06T 11/008 |

(Continued)

FOREIGN PATENT DOCUMENTS

| | | |
|---|---|---|
| JP | 2016059612 | 4/1916 |
| JP | 2013-99431 | 5/2013 |
| JP | 2013099431 A * | 5/2013 |

*Primary Examiner* — Mekonen T Bekele
(74) *Attorney, Agent, or Firm* — Andrew F. Young, Esq.; Lackenbach Siegel, LLP

(57) ABSTRACT

A DRR image generation method and a DRR image generation apparatus provide the equivalent image-quality to the X-ray radiograph and includes an image processing element 80, a calculation point setting element 81 that sets a ray connecting an X-ray tube relative to the geometrical arrangement of the X-ray radiography system reconstructed on a computer and each pixel of the X-ray CT data, and in addition, sets a plurality of calculation points on the ray; a CT value correction element 82 that compensates the CT value of each calculation point set by the calculation point setting element 81 based on the cumulative CT value from the X-ray tube to the calculation point; a CT value cumulation element 83 that cumulates the CT value of the calculation point located on the ray using the CT value of each calculation point after corrected by the CT value correction element 82; and a DRR image generation element 84 that that generates the DRR image based on the CT value cumulated by the CT value cumulation element 83.

15 Claims, 6 Drawing Sheets

(56) References Cited

U.S. PATENT DOCUMENTS

| | | | | |
|---|---|---|---|---|
| 2002/0097830 A1* | 7/2002 | Raupach | ............. | G01N 23/046 |
| | | | | 378/4 |
| 2003/0031299 A1* | 2/2003 | Ohishi | ................... | A61B 6/481 |
| | | | | 378/162 |
| 2006/0025681 A1* | 2/2006 | Abovitz | ................ | A61B 6/022 |
| | | | | 600/425 |
| 2007/0104317 A1* | 5/2007 | Ohishi | ................... | A61B 6/481 |
| | | | | 378/98.12 |
| 2007/0237288 A1* | 10/2007 | Tkaczyk | ............... | A61B 6/032 |
| | | | | 378/5 |
| 2008/0232546 A1* | 9/2008 | Stierstorfer | ........... | A61B 6/583 |
| | | | | 378/70 |
| 2011/0168878 A1* | 7/2011 | Hoerndler | .............. | G06T 11/005 |
| | | | | 250/252.1 |
| 2015/0154752 A1* | 6/2015 | Hirai | ........................ | G06T 7/32 |
| | | | | 382/132 |
| 2016/0148401 A1* | 5/2016 | Hirai | ..................... | G06T 11/008 |
| | | | | 382/131 |
| 2017/0055930 A1* | 3/2017 | Hagiwara | ................. | G06T 5/20 |
| 2018/0144510 A1* | 5/2018 | Lachaine | ............. | G06T 11/003 |

* cited by examiner

DRR IMAGE GENERATION METHOD AND DRR IMAGE GENERATION APPARATUS

CROSS REFERENCE TO RELATED APPLICATIONS

This application relates to, but does not claim priority from, JP 2014-190229 filed Sep. 17, 2014, the entire contents of which are incorporated herein by reference.

FIGURE SELECTED FOR PUBLICATION

FIG. 3

BACKGROUND OF THE INVENTION

Field of the Invention

The present invention relates to a DRR image generation method and particularly relates to the DRR image generation method and a DRR image generation apparatus that are applied to compare an X-ray radiograph that is radiographed by the X-ray radiography system comprising an X-ray tube and an X-ray detector when a radiation therapy is performed by irradiating a therapeutic beam to a subject.

Description of the Related Art

DRR (Digital Reconstructed Radiography) image that is a virtual fluoroscopic projection utilizing 3-dimensional image collected by an X-ray CT (computed or computer tomography) apparatus can be e.g., applied to positioning of a patient as the subject. Specifically, with regard to the therapy apparatus that performs the radiation therapy by irradiating the therapeutic beam to the patient, DRR image is applied to calculate a gap of the X-ray radiograph (image) when the positioning of the patient is completed. In addition, since the positioning of the patient is completed, a medical doctor and others make sure whether the positional gap between the DRR image and the X-ray radiograph is in an acceptable range or not by reading out such images.

When such DRR image is generated, a geometry that is a geometrical arrangement between the X-ray tube and the X-ray detector, which are sandwiching the CT image, is virtually reconstructed on the computer. And a line integral relative to a CT data voxel value on the line connecting between the virtual X-ray tube and the virtual X-ray detector is obtained. And a line integral of the CT value is converted to the line integral of a linear attenuation coefficient to calculate the X-ray attenuation, and then a relative X-ray dose that should reach to each pixel is calculated based on such attenuation. And a pixel value of each pixel is calculated to obtain the DRR image by executing normalization as to the relative X-ray dose (Patent Document 1).

RELATED PRIOR ART DOCUMENTS

Patent Document

Patent Document 1: JP Patent Published 2013-99431

ASPECTS AND SUMMARY OF THE INVENTION

In selected aspects of the present invention, there is provided a DRR image generation method and a DRR image generation apparatus capable of generating DRR image having the equivalent image-quality to the X-ray radiograph and tracking a moving subject dynamically even without a marker (marker-less dynamic tracking). An image processing element comprises: a calculation point setting element that sets a ray connecting the X-ray tube relative to the geometrical arrangement of the X-ray radiography system reconstructed on the computer and each pixel of the X-ray CT data, and in addition, sets a plurality of calculation points on the ray; a CT value correction element that compensates the CT value of each calculation point set by the calculation point setting element based on the cumulative CT value from the X-ray tube to the calculation point; a CT value cumulation element that cumulates the CT value of the calculation point located on the ray using the CT value of each calculation point after corrected by the CT value correction element; and a DRR image generation element that that generates the DRR image based on the CT value cumulated by the CT value cumulation element.

PROBLEMS TO BE SOLVED BY THE INVENTION

The DRR image is a single color X-ray with which no beam hardening phenomenon takes place and is generated under an ideal condition in which no scattering ray is radiographed. On the other hand, the beam hardening phenomenon or scattering ray takes place relative to the X-ray radiography actually utilizing the X-ray tube and the X-ray detector, so that image qualities of the DRR image and the X-ray radiograph would be different each other. Such difference between image qualities is particularly remarkable when radiograph a spine and so forth in which the beam hardening phenomenon is remarkable and many scattering rays exist.

If the image-quality between the DRR image and the X-ray radiograph is different, it can be hard to recognize the positional gap comparing the DRR image and the X-ray radiograph. In addition, even when e.g., the medical doctor determines whether the gap between the DRR image and the X-ray radiograph is in the acceptable range or not by reading out the images, such image reading-out may take a long time. In such case, not only it can be painful for the patient but also it can be problematic that a throughput of the radiation therapy using an expensive radiation therapy apparatus decrease.

The present invention is to provide solutions for the above set forth problems and provides a DRR image generation method and a DRR image generation apparatus capable of generating DRR image having the equivalent image-quality to the X-ray radiograph.

MEANS FOR SOLVING THE PROBLEM

According to an aspect of the first invention, a DRR image generation method that generates a DRR image that is applied to compare an X-ray radiograph that is radiographed by the X-ray radiography (imaging) system comprising an X-ray tube and an X-ray detector, when a radiation therapy is performed by irradiating the therapeutic beam to a subject and a positioning of the subject is completed, reconstructs a geometric arrangement of the X-ray radiography system on a computer and performing virtually a fluoroscopic projection on X-ray CT image data collected in advance, and also add the component corresponding to the beam hardening effect relative to a pixel value obtained based on the fluoroscopic projection.

According to an aspect of the second invention, the virtual fluoroscopic projection sets a ray connecting the X-ray tube and each pixel of the X-ray CT data relative to the geometric arrangement of the X-ray radiography system reconstructed on the computer, sets a plurality of calculation points on the ray, compensates the CT value of the calculation point based on the cumulative CT value from the X-ray tube to the calculation point, cumulates the CT value of the calculation point located on the ray using the CT value of each calculation point after correction, and generates the DRR image based on the cumulated CT value.

According to an aspect of the third invention, the pixel value thereof is corrected based on each pixel value obtained based on the fluoroscopic projection.

According to an aspect of the fourth invention, the correction is executed using a look-up table acquired in advance.

According to an aspect of the fifth invention, the look-up table is selected based on a spectrum of the X-ray irradiated from the X-ray tube.

According to an aspect of the sixth invention, the DRR image generation apparatus that generates a DRR image that is applied to compare an X-ray radiograph that is radiographed by the X-ray radiography system comprising an X-ray tube and an X-ray detector, when a radiation therapy is performed by irradiating the therapeutic beam to a subject and a positioning is completed, comprises an image processing element that reconstructs a geometric arrangement of the X-ray radiography system on a computer and performing virtually a fluoroscopic projection on X-ray CT image data collected in advance, and add also the component corresponding to the beam hardening effect relative to a pixel value obtained based on the fluoroscopic projection.

According to an aspect of the seventh invention, the DRR image generation method that generates a DRR image that is applied to compare an X-ray radiograph that is radiographed by the X-ray radiography system comprising an X-ray tube and an X-ray detector, when a radiation therapy is performed by irradiating the therapeutic beam to a subject and a positioning of the subject is completed, comprises an image processing element that reconstructs a geometric arrangement of the X-ray radiography system on a computer and performing virtually a fluoroscopic projection on X-ray CT image data collected in advance, and add also the component corresponding to the scattering ray that takes place in the X-ray radiography system.

According to an aspect of the eighth invention, the scattering ray distribution of the periphery of the pixel thereof is calculated from each pixel value obtained by the fluoroscopic projection and the scattering ray distribution thereof is added to each pixel value.

According to an aspect of the ninth invention, a calculation of the scattering ray distribution is executed using a look-up table acquired in advance.

According to an aspect of the tenth invention, the look-up table is selected based on a spectrum of the X-ray irradiated from the X-ray tube.

According to an aspect of the eleventh invention, the DRR image generation apparatus that generates a DRR image that is applied to compare an X-ray radiograph that is radiographed by the X-ray radiography system comprising an X-ray tube and an X-ray detector, when a radiation therapy is performed by irradiating the therapeutic beam to a subject and a positioning of the subject is completed, comprises an image processing element that reconstructs a geometric arrangement of the X-ray radiography system on a computer and performing virtually a fluoroscopic projection on X-ray CT image data collected in advance, and add also the component corresponding to the scattering ray in the X-ray radiography system relative to a pixel value obtained based on the fluoroscopic projection.

EFFECT OF THE INVENTION

According to the aspect of the first invention and the sixth invention, the component corresponding to the beam hardening effect is added to the pixel value obtained based on the fluoroscopic projection, so that a DRR image having the equivalent image-quality to the X-ray radiograph that is radiographed by the X-ray radiography system. Accordingly, the execution to read the images of the DRR image and the X-ray radiograph and the positioning can be facilitated.

According to the aspect of the second invention, the component corresponding to the beam hardening effect is added to the pixel value obtained based on the fluoroscopic projection, so that the DRR image having the equivalent image-quality to the X-ray radiograph that is radiographed by the X-ray radiography system can be generated by applying the same condition to the X-ray CT image on which the X-ray radiograph is performed.

According to the aspect of the third invention, the pixel per se is corrected on the basis of each pixel value obtained based on the fluoroscopic projection, so that a DRR image having the equivalent image-quality to the X-ray radiograph that is radiographed by the X-ray radiography system can be generated.

According to the aspect of the fourth invention and the fifth invention, the pixel value can be adequately and easily corrected utilizing the look-up table.

According to the aspect of the seventh invention and the eleventh invention, the component corresponding to the scattering ray, which takes place in the X-ray radiography system, is added to the pixel value obtained based on the fluoroscopic projection, so that a DRR image having the equivalent image-quality to the X-ray radiograph that is radiographed by the X-ray radiography system can be generated. Accordingly, the execution to read images of the DRR image and the X-ray radiograph and the positioning can be facilitated.

According to the aspect of the eight invention, the DRR image having the equivalent image-quality to the X-ray radiograph that is radiographed by the X-ray radiography system can be generated by utilizing the scattering ray distribution.

According to the aspect of the ninth invention and the tenth, the scattering ray distribution can be adequately and easily calculated utilizing the look-up table.

The above and other aspects, features and advantages of the present invention will become apparent from the following description read in conjunction with the accompanying drawings, in which like reference numerals designate the same elements.

DETAILED DESCRIPTION OF THE PREFERRED EMBODIMENTS

Figure 1:
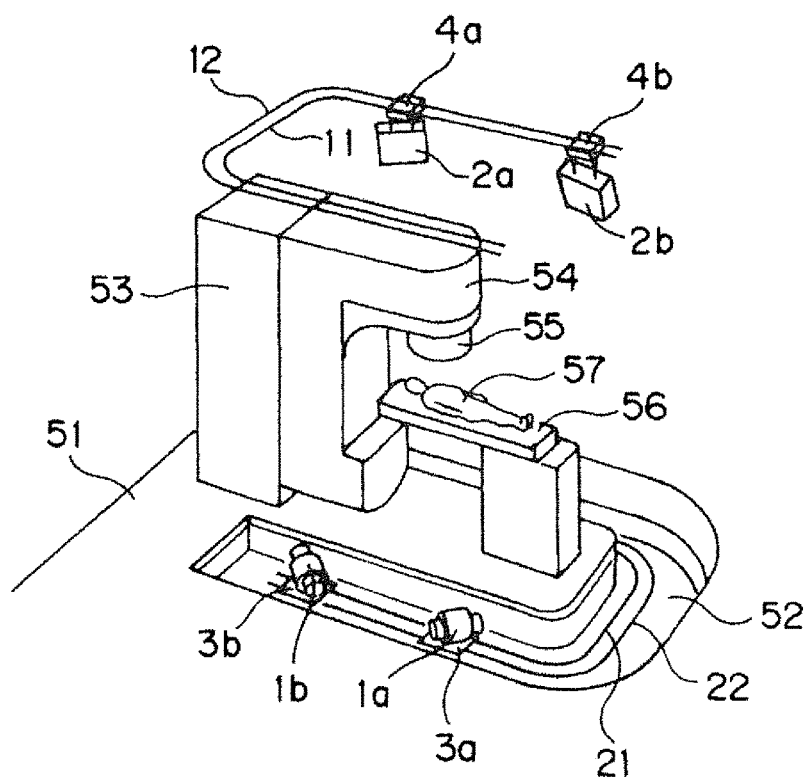
FIG. 1 is a schematic view illustrating an X-ray fluoroscopic apparatus and an X-ray therapeutic apparatus to which the DRR image generation method according to the aspect of the present invention is applied.

Reference will now be made in detail to embodiments of the invention. Wherever possible, same or similar reference numerals are used in the drawings and the description to refer to the same or like parts or steps. The drawings are in simplified form and are not to precise scale. The word 'couple', 'link', 'modifies' and similar terms do not necessarily denote direct and immediate connections, but also include connections through intermediate elements or devices. For purposes of convenience and clarity only, directional (up/down, etc.) or motional (forward/back, etc.) terms may be used with respect to the drawings. These and similar directional terms should not be construed to limit the scope in any manner. It will also be understood that other embodiments may be utilized without departing from the scope of the present invention, and that the detailed description is not to be taken in a limiting sense, and that elements may be differently positioned, or otherwise noted as in the appended claims without requirements of the written description being required thereto.

Various operations may be described as multiple discrete operations in turn, in a manner that may be helpful in understanding embodiments of the present invention; however, the order of description should not be construed to imply that these operations are order dependent or occur in separate structures, locations, or regions of a larger system.

As used herein, a "computer-based system" comprises an input device for receiving data, an output device for outputting data in tangible form (e.g. transmitting results to a further device, printing or displaying on a display screen), a permanent memory for storing data as well as computer code, and a microprocessor for executing computer code wherein said computer code resident in said permanent memory will physically cause said microprocessor to read-in data via said input device, process said data within said microprocessor and output said processed data via said output device.

It will be further understood by those of skill in the art that the apparatus and devices and the elements herein, without limitation, and including the sub components such as operational structures, circuits, communication pathways, and related elements, control elements of all kinds, display circuits and display systems and elements, any necessary driving elements, inputs, sensors, detectors, memory elements, processors and any combinations of these structures etc, as will be understood by those of skill in the art as also being identified as or capable of operating the systems and devices and subcomponents noted herein and structures that accomplish the functions without restrictive language or label requirements since those of skill in the art are well versed in related X-Ray and other diagnostic devices, computer and operational controls and technologies of radiographic devices and all their sub components, including various circuits and combinations of circuits without departing from the scope and spirit of the present invention.

Figure 2:
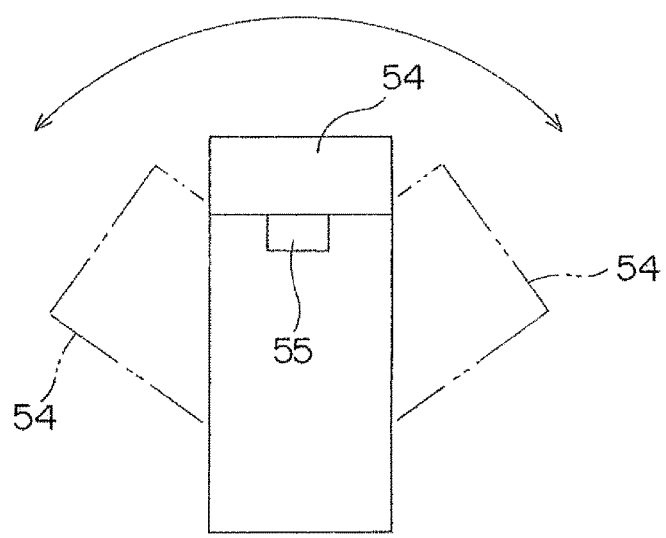
FIG. 2 is an explanatory drawing of the oscillating operation of the head 55 and the head support 54 relative to the radiation therapeutic apparatus.

The inventor sets forth Embodiments of the present invention based on the following FIGs.: FIG. 1 is a schematic view illustrating an X-ray fluoroscopic apparatus and an X-ray therapeutic apparatus to which the DRR image generation method according to the aspect of the present invention is applied. FIG. 2 is an explanatory drawing of the oscillating operation of the head 55 and the head support 54 relative to the radiation therapeutic device.

The radiation therapeutic apparatus that is to provide a therapeutic treatment by radiation of an X-ray or an electron beam to the affected area of the subject 57 lying on the table 56 comprises a gantry 53 installed on the floor 51 of the therapy room, a head support element 54 that oscillates around the axis facing the horizontal direction relative to the gantry 53 and a head 55 supported by the head support element 54 in order to irradiate the radiation to the subject 57. The head 55 can irradiate the radiation to the affected area of the subject 57 from a variety of angles because of the oscillating operation of the head support element 54.

On performing a radiation therapy, the radiation must be accurately irradiated to the affected area. For such purpose, a marker is set near the affected area. And relative to the X-ray fluoroscopic projection apparatus, the marker implanted inside the body is continuously looked at through the first X-ray fluoroscopic mechanism and the second X-ray fluoroscopic mechanism and the 3-dimensional position information as to the marker is calculated from the 2-dimensional fluoroscopic images obtained by the first X-ray fluoroscopic mechanism and the second X-ray fluoroscopic mechanism so that the marker can be structurally detected with a high degree of accuracy.

The X-ray fluoroscopic apparatus in order to perform such fluoroscopic operation comprises the first X-ray fluoroscopic mechanism consisting of the first X-ray tube 1a and the first X-ray detector 2a and the second X-ray fluoroscopic mechanism consisting of the second X-ray tube 1b and the second X-ray detector 2b, and further comprises the moving mechanism that moves the first X-ray tube 1a and the first X-ray detector 2a to the first fluoroscopic position and the second fluoroscopic position, as described later, so as to be in-place facing each other and also the second X-ray tube 1b and the second X-ray detector 2b to the first fluoroscopic position and the second fluoroscopic position so as to be in-place facing each other. Further, for example, a flat panel detector (FPD) is used as the first X-ray detector 2a and the second X-ray detector 2b.

The first X-ray tube 1a is supported with the first pedestal 3a for the X-ray tube. Further, the second X-ray tube 1b is supported with the second pedestal 3b for the X-ray tube. The first rail 21 for the X-ray tube having approximately U-shape, in which two linear portions are connected with the connection element including a circular portion, and the second rail 22 for the X-ray tube having approximately U-shape as the same as the first rail 21 for the X-ray tube, in which two linear portions are connected with the connection element including a circular portion, are installed on the bottom surface 52 of the concave portion formed on the floor 51 in the radiography room. The first rail 21 and second rail 22 for the X-ray tube for such X-ray tubes are parallel in-place each other. Then, the first pedestal 3a for the X-ray tube and the second pedestal 3b for the X-ray tube move to a plurality of fluoroscopy positions by being guided with the first rail 21 and the second rail 22, The first X-ray detector 2a is supported with the first pedestal 4a for the X-ray detector. Further, the second X-ray detector 2b is supported with the second pedestal 4b for the X-ray detector. The first rail 11 for the X-ray detector having approximately U-shape, in which two linear portions are connected to the connection element including a circular portion, and the second rail 12 for the X-ray tube having approximately U-shape as the same as the first rail 11 for the X-ray tube, in which two linear portions are connected to the connection element including a circular portion, are suspended from the ceiling of the radiography room. The first rail 11 for the X-ray detector and the second rail 12 for the X-ray detector are parallel in-place each other. Then, the first pedestal 4a for the X-ray detector and the second pedestal 4b for the X-ray detector move to a plurality of fluoroscopy positions by being guided with the first rail 11 and the second rail 12.

Relative to such radiation therapy apparatus and the X-ray fluoroscopic apparatus, the X-ray radiograph of the subject 57 actually imaged using the X-ray fluoroscopic apparatus and the DRR image obtained from the data relative to the CT image of the subject 57 when the radiation treatment planning is prepared must be compared in order to set the subject 57 in-place in the correct location and execute the radiation therapy. At this time, the beam hardening phenomenon or the scattering ray takes place relative to the X-ray radiograph actually utilizing the X-ray tube and the X-ray detector, so that image-qualities of the DRR image and the X-ray radiograph would be different each other. Therefore, according to the aspect of the present invention, the image processing element 80 that generates the DRR image having the equivalent image-quality to the X-ray radiograph under considering the beam hardening effect and the effect of the scattering ray is adopted.

Figure 3:
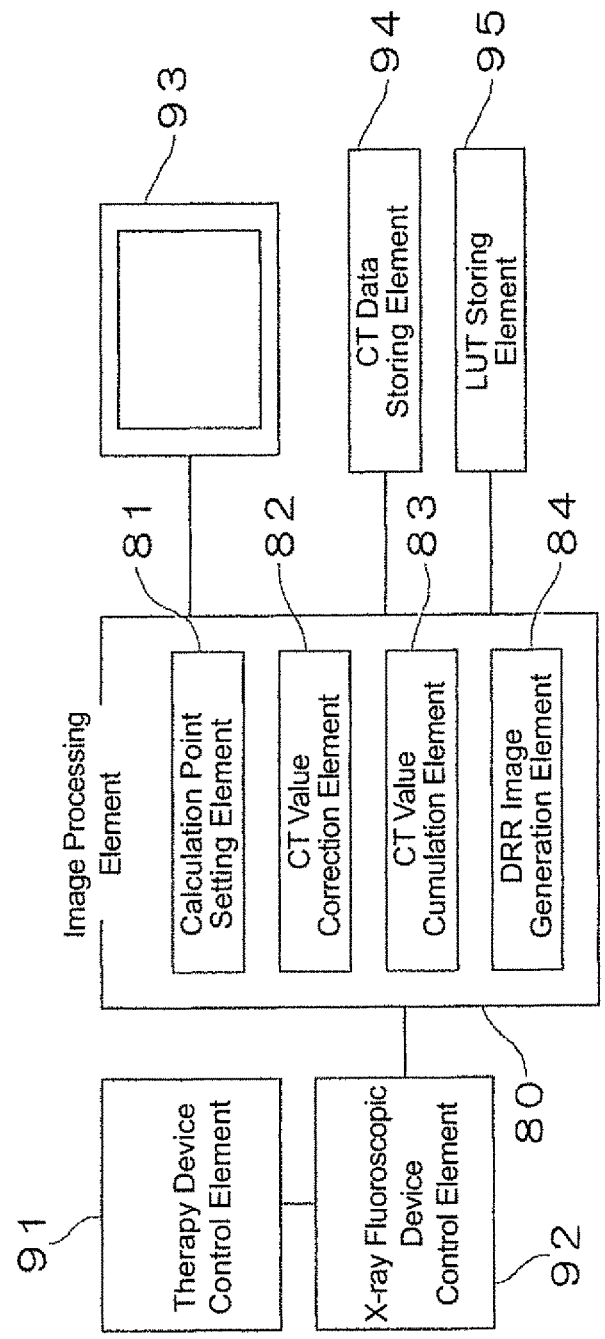
FIG. 3 is a block diagram illustrating a control system comprising an image processing element 80 according to the aspect of the Embodiment 1 of the present invention.

FIG. 3 is a block diagram illustrating a control system comprising an image processing element 80 according to the aspect of the Embodiment 1 of the present invention.

The radiation therapy apparatus comprises a radiation therapy control element that controls the head 55, the head support element 54 and the gantry 53 and so forth as set forth above. In addition, the X-ray fluoroscopic apparatus comprises the first X-ray tube 1a, the second X-ray tube 1b, the first X-ray detector 2a and the second X-ray detector 2b, and further comprise an X-ray fluoroscopic apparatus control element 92 that controls a moving mechanism that moves the first X-ray tube 1a, the second X-ray tube 1b, the first X-ray detector 2a and the second X-ray detector 2b. The therapy apparatus control element 91 and the X-ray fluoroscopic apparatus control element 92 are connected to each other.

The X-ray fluoroscopic radiograph control element 92 is connected to the image processing element 80 and displays the X-ray fluoroscopic image on the display 93 comprising the liquid crystal display panel and so forth via the image processing element 80. The image processing element 80 can acquire the CT data obtained by CT imaging the subject 57 when the radiation treatment planning is prepared from the CT data storing element 94. In addition, the image processing element 80 can acquire the data in the look-up table used when the DRR image is generated, described later, from the look-up data table storing element 95. Further, the X-ray fluoroscopic apparatus 92 and the image processing element 80 comprises: a computer including a CPU that executes the logic operation; a ROM that stores operation programs required to control the apparatus; and a RAM that stores temporally the data and so forth.

The image processing element 80 comprises: a calculation point setting element 81 that sets a ray connecting the X-ray tube relative to the geometrical arrangement of the X-ray radiography system reconstructed on the computer and each pixel of the X-ray CT data, and in addition, sets a plurality of calculation points on the ray; a CT value correction element 82 that corrects the CT value of each calculation point set by the calculation point setting element 81 based on the cumulative CT value from the X-ray tube to the calculation point; a CT value cumulation element 83 that cumulates the CT value of the calculation point located on the ray using the CT value of each calculation point after corrected by the CT value correction element 82; and a DRR image generation element 84 that that generates the DRR image based on the CT value cumulated by the CT value cumulation element 83.

When the DRR image is generated by the image processing element 80, a geometry that is a geometric arrangement of an X-ray radiography system on a computer is reconstructed and a fluoroscopic projection on the X-ray CT image data collected in advance; is virtually performed.

Figure 4:
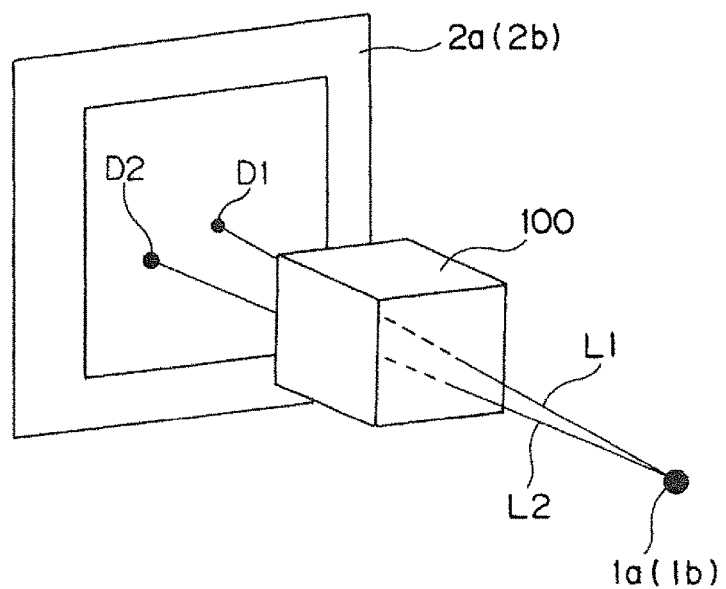
FIG. 4 is an explanatory drawing illustrating schematically the aspect of the virtual fluoroscopic projection.

FIG. 4 is the explanatory drawing illustrating schematically the aspect of the virtual fluoroscopic projection.

When the DRR image is generated, 3-dimensional CT data 100 are in-place on the computer. And the geometry that is a geometric arrangement of the X-ray radiography system on the computer is reconstructed. According to the aspect of the present Embodiment 1, referring to FIG. 1, the first X-ray tube 1a or the second X-ray tube 1b and the first X-ray detector 2a and the second X-ray detector 2b are in-place at both sides as if sandwiching the X-ray CT data 100. Referring to FIG. 3, the X-ray CT data 100 are obtained from the CT data storing element 94. The arrangement of such X-ray CT data 100 and the first X-ray tube 1a or the second X-ray tube 1b and the first X-ray detector 2a and the second X-ray detector 2b have the same geometry as the arrangement of the subject 57 on performing a fluoroscopy using the X-ray fluoroscopic apparatus, referring to FIG. 1, and the first X-ray tube 1a or the second X-ray tube 1b and the first X-ray detector 2a and the second X-ray detector 2b. Here, the geometry means a geometrical arrangement relationship between the radiography target and the X-ray tube and the X-ray detector.

Under such condition, a number of rays connecting the first X-ray tube 1a or the second X-ray tube 1b and the first X-ray detector 2a or the second X-ray detector 2b via each pixel of the X-ray CT data 100 are set by the calculation point element 81 relative to the image processing element 80. In addition, referring to FIG. 4, two rays L1, L2 are shown for the explanation of convenience. And a plurality of calculation points is respectively set on such ray L. Such calculation point is incremented by e.g., 1 mm on the ray by the calculation point setting element 81.

Next, the CT value of each calculation point set by the calculation point setting element 81 is calculated by executing a linear interpolation and so forth. And such CT value is corrected by the CT value correction element 82 based on the cumulative CT value from the first X-ray tube 1a or the second X-ray tube 1b relative to the ray L to each calculation point. When such correction is executed, the look-up table stored in the look-up table storing element 95 referring to FIG. 3 is applied. A coefficient that corrects the CT value is stored in the look-up table in which the cumulative CT value is an index. Relative to such look-up table, the larger cumulative CT value is, the smaller coefficient is.

The beam hardening phenomenon is the phenomenon in which the X-ray hardly attenuates due to the high-energy part of the X-ray spectrum relatively increased along with attenuation of the X-ray passing through the subject 57 because the X-ray applied to the X-ray fluoroscopy is a continuous X-ray. Therefore, if it is set as the larger the cumulative CT value is, the smaller the coefficient to correct the CT value is, the same level of correction as the beam hardening effect becomes feasible. Such look-up table can be obtained by an actual measurement or by a simulation, in advance. A plurality of such look-up tables is stored in the look-up table storing element 95 so that the look-up table can cover the case when the tube voltages are different and/or the case when the X-ray spectra irradiated from the first X-ray tube or the second X-ray tube vary. And the most adequate look-up table can be selected based on a spectrum of the X-ray actually used for radiograph.

Next, a line integral that cumulates the CT values of each calculation point on the ray after corrected by the CT value correction element 82 is executed by the CT value cumulation element 83. And the DRR image is generated by the DRR image generation element 84 while calculating the X-ray attenuation by converting the cumulated CT value to the line integral of the line attenuation coefficient.

According to the aspect of the present Embodiment, the CT values of a plurality of calculation points set on each ray are corrected based on the cumulated CT value from the first X-ray tube 1a or the second X-ray tube 1b to each calculation point, the component corresponding to the beam hardening effect can be added to the pixel value obtained based on the fluoroscopic projection by cumulating the CT value of the calculation point positioned on each ray using the CT value of each calculation point after correction, so that a DRR image having the equivalent image-quality to the X-ray radiograph that is radiographed by the X-ray radiography system can be generated.

Figure 5:
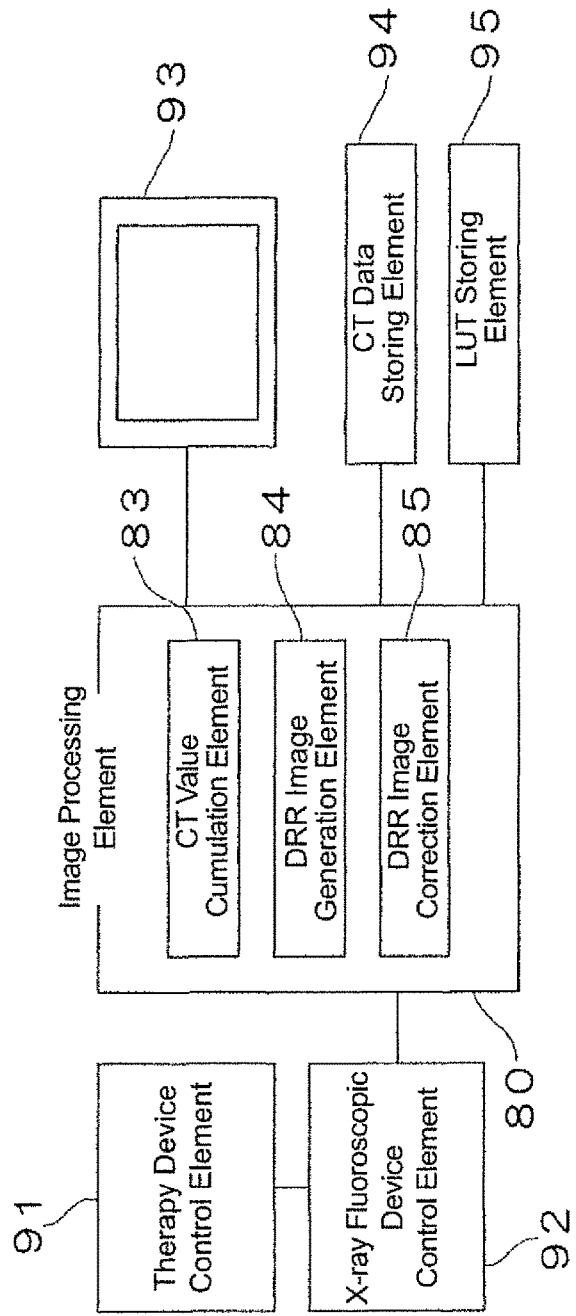
FIG. 5 is a block diagram illustrating a control system comprising an image processing element 80 according to the aspect of the Embodiment 2 of the present invention.

Next, the inventor sets forth the other Embodiment of the present invention. FIG. 5 is a block diagram illustrating a control system comprising an image processing element 80 according to the aspect of the Embodiment2 of the present invention. Further, the same member as illustrated according to the aspect of the Embodiment 1 set forth above is not set forth while providing the identical reference sign.

As a functional element, the image processing element 80 comprises: a CT value cumulating element 83 that cumulates the CT value while setting the above described ray L relative to the geometric arrangement of the X-ray radiography system reconstructed on the computer; a DRR image generation element 84 that generates the DRR image based on the CT value cumulated by the CT value cumulating element 83; and a DRR image correction element 85 that adds the component corresponding to the beam hardening effect relative to each pixel value of the DRR image.

Also, referring to FIG. 4, according to the aspect of the present Embodiment, when the DRR image is generated, 3-dimensional CT data 100 are in-place on the computer. And the geometry that is a geometric arrangement of the X-ray radiography system on the computer is reconstructed. Also, according to the aspect of the present Embodiment, referring to FIG. 1, the first X-ray tube 1a or the second X-ray tube 1b and the first X-ray detector 2a and the second X-ray detector 2b are in-place at both sides as if sandwiching the X-ray CT data 100. Referring to FIG. 3, the X-ray CT data 100 are obtained from the CT data storing element 94. The arrangement of such X-ray CT data 100 and the first X-ray tube 1a or the second X-ray tube 1b and the first X-ray detector 2a and the second X-ray detector 2b have the same geometry as the arrangement of the subject 57 on performing a fluoroscopy using the X-ray fluoroscopic apparatus, referring to FIG. 1, and the first X-ray tube 1a or the second X-ray tube 1b and the first X-ray detector 2a and the second X-ray detector 2b.

Under such condition, as well as the Embodiment 1, a number of rays L connecting the first X-ray tube 1a or the second X-ray tube 1b and the first X-ray detector 2a or the second X-ray detector 2b via each pixel of the X-ray CT data 100 are set. And the line integration is executed by cumulating the CT value on the ray L by the CT cumulating element 83. And the DRR image is generated by the DRR image generation element 84 while calculating the X-ray attenuation by converting the cumulated CT value to the line integral of the line attenuation coefficient. And the correction in which the component corresponding to the beam hardening effect is added to each pixel of the generated DRR image by the DRR image correction element 85.

Further specifically, the pixel value of the DRR image generated by the DRR image generation element 84 is converted to a larger pixel value in which the component corresponding to the beam hardening effect is added thereto. When such correction is executed, the look-up table stored in the look-up table storing element 95 referring to FIG. 5 is applied. Such look-up table stores the relationship between the pixel value of the DRR image, which is obtained by an actual measurement or a simulation, and the pixel value corresponding to the beam hardening effect at the time. In addition, a plurality of such look-up tables are stored in the look-up table storing element 95 so that the look-up table can cover the case when the tube voltages are different and/or the case when the X-ray spectra irradiated from the first X-ray tube 1a or the second X-ray tube 1b vary. And the most adequate look-up table can be selected based on a spectrum of the X-ray actually used for radiography.

An image processing apparatus according to the aspect of the Embodiment 2 can add the component corresponding to the beam hardening effect to the pixel value obtained based on the fluoroscopic projection by correcting the pixel value thereof based on each pixel value obtained by the fluoroscopic projection. According to the aspect of the eight invention, the DRR image having the equivalent image-quality to the X-ray radiograph that is radiographed by the X-ray radiography system can be generated by utilizing the scattering ray distribution.

Figure 6:
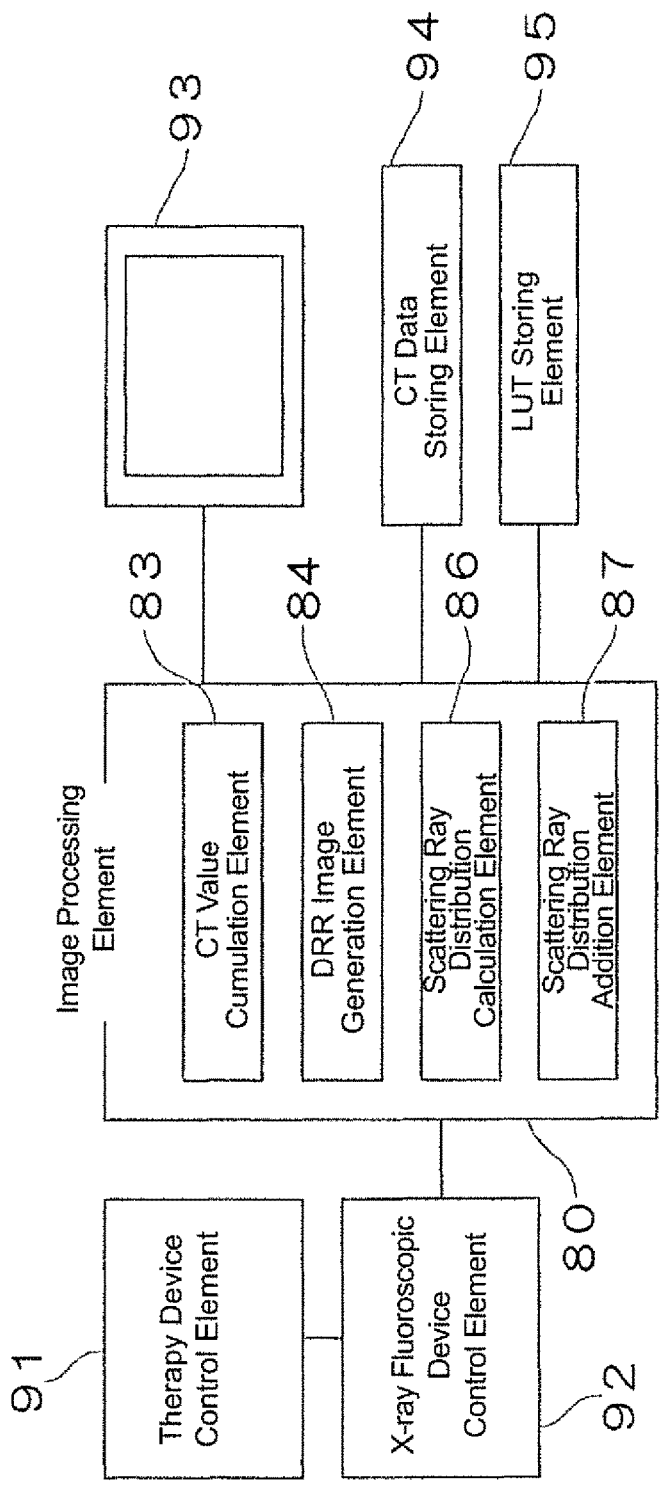
FIG. 6 is a block diagram illustrating a control system comprising an image processing element 80 according to the aspect of the Embodiment 3 of the present invention.

Next, the inventor sets forth the other Embodiment of the present invention. FIG. 6 is a block diagram illustrating a control system comprising an image processing element 80 according to the aspect of the Embodiment 3 of the present invention. Further, the same constitution as illustrated in the above described Embodiment 1, Embodiment 2 is not described in detail while providing the identical reference letter.

As a functional element, the image processing element 80 comprises: a CT value cumulating element 83 that cumulates the CT value while setting the above described ray L relative to the geometric arrangement of the X-ray radiography system reconstructed on the computer; a DRR image generation element 84 that generates the DRR image based on the CT value cumulated by the CT value cumulating element 83; a scattering ray distribution calculation element 86 that calculates a scattering ray distribution of the periphery of the pixel thereof from each pixel value of the DRR image generated by the DRR image element 84; and a scattering ray distribution addition element 87 that adds the scattering distribution calculated by the scattering ray distribution calculation element 86 to each pixel value of the DRR image generated by the DRR image generation element 84.

Also, referring to FIG. 4, according to the aspect of the present Embodiment, when the DRR image is generated, 3-dimensional CT data 100 are in-place on the computer. And the geometry that is a geometric arrangement of the X-ray radiography system on the computer is reconstructed. Also, according to the aspect of the present Embodiment, referring to FIG. 1, the first X-ray tube 1a or the second X-ray tube 1b and the first X-ray detector 2a and the second X-ray detector 2b are in-place at both sides as if sandwiching the X-ray CT data 100. Referring to FIG. 3, the X-ray CT data 100 are obtained from the CT data storing element 94. The arrangement of such X-ray CT data 100 and the first X-ray tube 1a or the second X-ray tube 1b and the first X-ray detector 2a and the second X-ray detector 2b have the same geometry as the arrangement of the subject 57 on performing a fluoroscopy using the X-ray fluoroscopic device, referring to FIG. 1, and the first X-ray tube 1a or the second X-ray tube 1b and the first X-ray detector 2a and the second X-ray detector 2b.

Under such condition, a number of rays connecting the first X-ray tube 1a or the second X-ray tube 1b and the first X-ray detector 2a or the second X-ray detector 2b via each pixel of the X-ray CT data 100 are set. And the line integration is executed by cumulating the CT value on the ray L by the CT cumulating element 83. And the DRR image is generated by the DRR image generation element 84 while calculating the X-ray attenuation by converting the cumulated CT value to the line integral of the line attenuation coefficient. And the component corresponding to the scattering ray taking place in the X-ray radiography system is added to each pixel of the generated DRR image.

More specifically, the scattering ray distribution of the periphery of the pixel is obtained by the scattering ray distribution calculation element 86 relative to each pixel of the DRR image generated by the DRR image generation element 84. Referring to FIG. 6, when such correction is executed, the look-up table stored in the look-up table storing element 95 is applied to calculate the scattering ray distribution. Such look-up table stores the relationship between the pixel value of the DRR image, which is obtained by an actual measurement or a simulation, and the scattering ray distribution of the peripheral pixel thereof. Such scattering ray distribution is stored as a peaked-point spread function. And the shape of such peaked-point spread function can be obtained by the actual measurement or the simulation as set forth above. In addition, a plurality of such look-up tables is stored in the look-up table storing element 95 so that the look-up table can cover the case when the tube voltages are different and/or the case when the X-ray spectra irradiated from the first X-ray tube or the second X-ray tube vary. And the most adequate look-up table can be selected based on a spectrum of the X-ray actually used for radiography.

An image processing apparatus according to the aspect of the Embodiment 3 can add the component corresponding to the scattering ray to the pixel value obtained based on the fluoroscopic projection by compensating the pixel value thereof based on each pixel value obtained by the fluoroscopic projection. Therefore, the DRR image having the equivalent image-quality to the X-ray radiograph that is radiographed by the X-ray radiography system can be generated.

INDUSTRIAL APPLICABILITY

The present invention is applicable when a DRR image is generated in e.g., a radiation therapy and so forth.

REFERENCE OF SIGNS

1a First X-ray tube
1b Second X-ray tube
2a First X-ray detector
2a Second X-ray detector
53 Gantry
54 Head support element
55 Head
56 Table
57 Subject
80 Image processing element
81 Calculation point set-up element
82 CT value correction element
83 CT value cumulation element
84 DRR image generation element
85 DRR image correction element
86 Scattering ray distribution calculation element
87 Scattering ray distribution addition element
91 Therapy device control element
92 X-ray fluoroscopic device control element
93 Display element
94 CT data storing element
95 Look-up table storing element
100 X-ray CT data Although only a few embodiments have been disclosed in detail above, other embodiments are possible and the inventors intend these to be encompassed within this specification. The specification describes certain technological solutions to solve the technical problems that are described expressly and inherently in this application. This disclosure describes embodiments, and the claims are intended to cover any modification or alternative or generalization of these embodiments which might be predictable to a person having ordinary skill in the art.

Those of skill would further appreciate that the various illustrative logical blocks, modules, circuits, and algorithm steps described in connection with the embodiments disclosed herein may be implemented as electronic hardware, computer software running on a specific purpose machine that is programmed to carry out the operations described in this application, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the exemplary embodiments.

The various illustrative logical blocks, modules, elements, and circuits described in connection with the embodiments disclosed herein, may be implemented or performed with a general or specific purpose processor, or with hardware that carries out these functions, e.g., a Digital Signal Processor (DSP), an Application Specific Integrated Circuit (ASIC), a Field Programmable Gate Array (FPGA) or other programmable logic device, discrete gate or transistor logic, discrete hardware components, or any combination thereof designed to perform the functions described herein. A general purpose of processor may be a microprocessor, but in the alternative, the processor may be any conventional processor, controller, microcontroller, or solid-state machine. The processor can be part of a computer system that also has an internal bus connecting to cards or other hardware, running based on a system BIOS or equivalent that contains startup and boot software, system memory which provides temporary storage for an operating system, drivers for the hardware and for application programs, disk interface which provides an interface between internal storage device(s) and the other hardware, an external peripheral controller which interfaces to external devices such as a backup storage device, and a network that connects to a hard wired network cable such as Ethernet or may be a wireless connection such as a RF link running under a wireless protocol such as 802.11. Likewise, an external bus may be any of but not limited to hard wired external busses such as IEEE-1394 or USB. The computer system can also have a user interface port that communicates with a user interface, and which receives commands entered by a user, and a video output that produces its output via any kind of video output format, e.g., VGA, DVI, HDMI, display port, or any other form. This may include laptop or desktop computers, and may also include portable computers, including cell phones, tablets such as the IPAD™ and Android™ platform tablet, and all other kinds of computers and computing platforms.

A processor may also be implemented as a combination of computing devices, e.g., a combination of a DSP and a microprocessor, a plurality of microprocessors, one or more microprocessors in conjunction with a DSP core, or any other such configuration. These devices may also be used to select values for devices as described herein.

The steps of a method or algorithm described in connection with the embodiments disclosed herein may be embodied directly in hardware, in a software module executed by a processor, using cloud computing, or in combinations. A software module may reside in Random Access Memory (RAM), flash memory, Read Only Memory (ROM), Electrically Programmable ROM (EPROM), Electrically Erasable Programmable ROM (EEPROM), registers, hard disk, a removable disk, a CD-ROM, or any other form of tangible storage medium that stores tangible, non-transitory computer based instructions. An exemplary storage medium is coupled to the processor such that the processor can read information from, and write information to, the storage medium. In the alternative, the storage medium may be integral to the processor. The processor and the storage medium may reside in reconfigurable logic of any type.

In one or more exemplary embodiments, the functions described may be implemented in hardware, software, firmware, or any combination thereof. If implemented in software, the functions may be stored on or transmitted over as one or more instructions or code on a computer-readable medium. Computer-readable media includes both computer storage media and communication media including any medium that facilitates transfer of a computer program from one place to another. A storage media may be any available media that can be accessed by a computer. By way of example, and not limitation, such computer-readable media can comprise RAM, ROM, EEPROM, CD-ROM or other optical disk storage, magnetic disk storage or other magnetic storage devices, or any other medium that can be used to carry or store desired program code in the form of instructions or data structures and that can be accessed by a computer.

The memory storage can also be rotating magnetic hard disk drives, optical disk drives, or flash memory based storage drives or other such solid state, magnetic, or optical storage devices. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, includes compact disc (CD), laser disc, optical disc, digital versatile disc (DVD), floppy disk and blu-ray disc where disks usually reproduce data magnetically, while discs reproduce data optically with lasers. Combinations of the above should also be included within the scope of computer-readable media. The computer readable media can be an article comprising a machine-readable non-transitory tangible medium embodying information indicative of instructions that when performed by one or more machines result in computer implemented operations comprising the actions described throughout this specification.

Operations as described herein can be carried out on or over a web site. The website can be operated on a server computer, or operated locally, e.g., by being downloaded to the client computer, or operated via a server farm. The website can be accessed over a mobile phone or a PDA, or on any other client. The website can use HTML code in any form, e.g., MHTML, or XML, and via any form such as cascading style sheets ("CSS") or other.

The computers described herein may be any kind of computer, either general purpose, or some specific purpose computer such as a workstation, or remote-based or cloud-based including applications (APPs) linked with cloud-based or remote based computers. The programs may be written in C, or Java, Brew or any other programming language now known or later developed. The programs may be resident on a storage medium, e.g., magnetic or optical, e.g. the computer hard drive, a removable disk or media such as a memory stick or SD media, or other removable medium. The programs may also be run over a network, for example, with a server or other machine sending signals to the local machine, which allows the local machine to carry out the operations described herein.

Also, the inventors intend that only and solely those claims which use the words "means for" are intended to be interpreted under 35 USC 112, sixth paragraph. Moreover, no limitations from the specification are intended to be read into any claims, unless those limitations are expressly included in the claims.

Having described at least one of the preferred embodiments of the present invention with reference to the accompanying drawings, it will be apparent to those skills that the invention is not limited to those precise embodiments, and that various modifications and variations can be made in the presently disclosed system without departing from the scope or spirit of the invention. Thus, it is intended that the present disclosure cover modifications and variations of this disclosure provided they come within the scope of the appended claims and their equivalents.

What is claimed is:

1. A DRR image generation method, that generates a DRR image, comprising the steps of:
   reconstructing a geometric arrangement of the X-ray radiography system on a computer;
   providing an an X-ray tube and an X-ray detector in said geometric arrangement;
   providing a DRR image generation apparatus in said geometric arrangement, the DRR image generation apparatus able to generate a DRR image;
   performing virtually a fluoroscopic projection on X-ray CT radiographic data collected in advance; and
   generating the DRR image on which the component corresponding to the beam hardening effect is added, simultaneously conducting a step of adding a component corresponding to a beam hardening effect to a pixel value obtained by said fluoroscopic projection as the DRR image is generated.

2. The DRR image generation method, according to claim 1, wherein:
said DRR image is applied to be compared with an X-ray radiograph that is radiographed by said X-ray radiography system comprising an X-ray tube and an X-ray detector, when a radiation therapy is performed by irradiating a therapeutic beam.

3. The DRR image generation method, according to claim 1, further comprising the steps of:
setting a ray connecting said X-ray tube and each pixel of said X-ray CT data relative to the geometric arrangement of said X-ray radiography system reconstructed on said computer, and a plurality of calculation points on said ray by said virtual fluoroscopic projection;
correcting a CT value at said calculation point based on a cumulated CT value from said X-ray tube to said calculation point;
cumulating said CT value of said calculation point located on said ray using the CT value of each calculation point after correction; and
generating said DRR image based on the cumulated CT value.

4. The DRR image generation method, according to claim 1, further comprising the step of:
correcting a pixel value thereof based on each pixel value obtained based on said fluoroscopic projection.

5. The DRR image generation method, according to claim 3, further comprising a step of:
executing said correction using a look-up table acquired in advance.

6. The DRR image generation method, according to claim 4, further comprising the step of:
selecting said look-up table based on a spectrum of the X-ray irradiated from said X-ray tube.

7. A DRR image generation apparatus, that generates a DRR image comprising:
an image processing element that: reconstructs a geometric arrangement of an X-ray radiography system including at least one X-ray tube and at least one X-ray detector on a computer; performs virtually a fluoroscopic projection on X-ray CT image data collected in advance; and adds a component corresponding to a beam hardening effect to a pixel value obtained based on said fluoroscopic projection simultaneously when the DRR image is generated whereby said DRR image has a pixel value including the component corresponding to the beam hardening effect.

8. The DRR image generation apparatus, according to claim 7, wherein:
the DRR image generation apparatus is applied to be compared with an X-ray radiograph that is radiographed by said X-ray radiography system comprising an X-ray tube and an X-ray detector, when a radiation therapy is performed by irradiating a therapeutic beam to a subject and a positioning is completed.

9. A DRR image generation method, that generates a DRR image comprising the steps of:
reconstructing a geometric arrangement of an X-ray radiography system on a computer;
providing a DRR image generation apparatus, the DRR image generation apparatus able to generate the DRR image;
performing virtually a fluoroscopic projection on X-ray CT radiographic data collected in advance; and
simultaneously adding a component corresponding to a scattering ray taking place in said X-ray radiography system when the DRR image is generated.

10. The DRR image generation method, according to claim 9, wherein:
said DRR image is applied to be compared with an X-ray radiograph that is radiographed by said X-ray radiography system comprising an X-ray tube and an X-ray detector, when a radiation therapy is performed by irradiating a therapeutic.

11. The DRR image generation method, according to claim 7, further comprising the steps of:
calculating the scattering ray distribution of the periphery of the pixel of each pixel from each pixel value obtained based on said fluoroscopic projection; and
adding said scattering ray distribution to said each pixel value.

12. The DRR image generation method, according to claim 8, further comprising the step of:
executing a calculation of said scattering ray distribution using a look-up table acquired in advance.

13. The DRR image generation method, according to claim 9, further comprising the step of:
selecting said look-up table based on a spectrum of the X-ray irradiated from said X-ray tube.

14. A DRR image generation apparatus, that generates a DRR image, comprising:
an image processing element that upon performance: reconstructs a geometric arrangement of an X-ray radiography system including at least one X-ray tube and at least one X-ray detector on a computer, and performs virtually a fluoroscopic projection on X-ray CT image data collected in advance; and simultaneously adds a component corresponding to a scattering beam effect taking place in said X-ray radiography system when the DRR image is generated whereby said DRR image has a pixel value including the component corresponding to the scattering beam effect.

15. The DRR image generation apparatus, according to claim 14, wherein:
said DRR image is applied to be compared with an X-ray radiograph that is radiographed by said X-ray radiography system comprising an X-ray tube and an X-ray detector, when a radiation therapy is performed by irradiating a therapeutic beam.

* * * * *